(12) United States Patent
Lin

(10) Patent No.: US 6,928,858 B2
(45) Date of Patent: Aug. 16, 2005

(54) APPARATUS AND METHOD FOR THERMAL CONDUCTIVITY DETECTION IN GAS CHOMATOGRAPHY EQUIPMENT

(75) Inventor: Bingyi Lin, Shanghai (CN)

(73) Assignee: Agilent Technologies, Inc., Palo Alto, CA (US)

( * ) Notice: Subject to any disclaimer, the term of this patent is extended or adjusted under 35 U.S.C. 154(b) by 18 days.

(21) Appl. No.: 10/479,645

(22) PCT Filed: Jan. 29, 2003

(86) PCT No.: PCT/CN03/00100

§ 371 (c)(1),
(2), (4) Date: Dec. 2, 2003

(87) PCT Pub. No.: WO2004/068134

PCT Pub. Date: Aug. 12, 2004

(65) Prior Publication Data

US 2004/0250601 A1 Dec. 16, 2004

(51) Int. Cl.[7] .......................... G01N 30/66; G01N 27/18
(52) U.S. Cl. .................... 73/25.03; 73/23.35; 73/25.01; 73/25.05; 96/101; 96/105; 96/106; 422/83; 422/89
(58) Field of Search .............................. 73/23.35, 23.4, 73/23.42, 25.01, 25.03, 25.05, 61.41, 61.52, 61.57; 95/82, 85, 87; 96/101, 105, 106; 422/68.1, 70, 83, 89

(56) References Cited

U.S. PATENT DOCUMENTS

| | | | | |
|---|---|---|---|---|
| 2,585,959 A | * | 2/1952 | Minter | 73/25.03 |
| 3,474,660 A | * | 10/1969 | Dooley | 73/25.04 |
| 3,603,134 A | * | 9/1971 | Norem | 73/25.04 |
| 4,185,490 A | * | 1/1980 | Clouser et al. | 73/23.35 |
| 4,316,381 A | * | 2/1982 | Woodruff | 73/31.05 |
| 4,464,925 A | * | 8/1984 | Kolloff | 73/23.4 |
| 4,594,879 A | * | 6/1986 | Maeda et al. | 73/25.04 |
| 5,551,283 A | * | 9/1996 | Manaka et al. | 73/31.01 |
| 6,550,961 B1 | * | 4/2003 | Ueda | 374/44 |
| 6,623,699 B1 | * | 9/2003 | Pack et al. | 422/80 |

FOREIGN PATENT DOCUMENTS

JP        01088364 A    *    4/1989        G01N/30/66

* cited by examiner

*Primary Examiner*—Hezron Williams
*Assistant Examiner*—David A. Rogers

(57) ABSTRACT

A thermal conductivity detector includes separate sample gas and reference gas chambers. Each chamber has a gas inlet and a gas outlet and a sensor. The chambers are connected by at least one passageway. For example, a passageway can extend from the sample gas chamber to the reference gas chamber adjacent the gas inlets. As a further example, a passageway can be provided adjacent the gas outlets. More specifically, an exhaust passageway extends from the first passageway to the additional passageway and there is an exhaust outlet connected to the additional passageway.

8 Claims, 5 Drawing Sheets

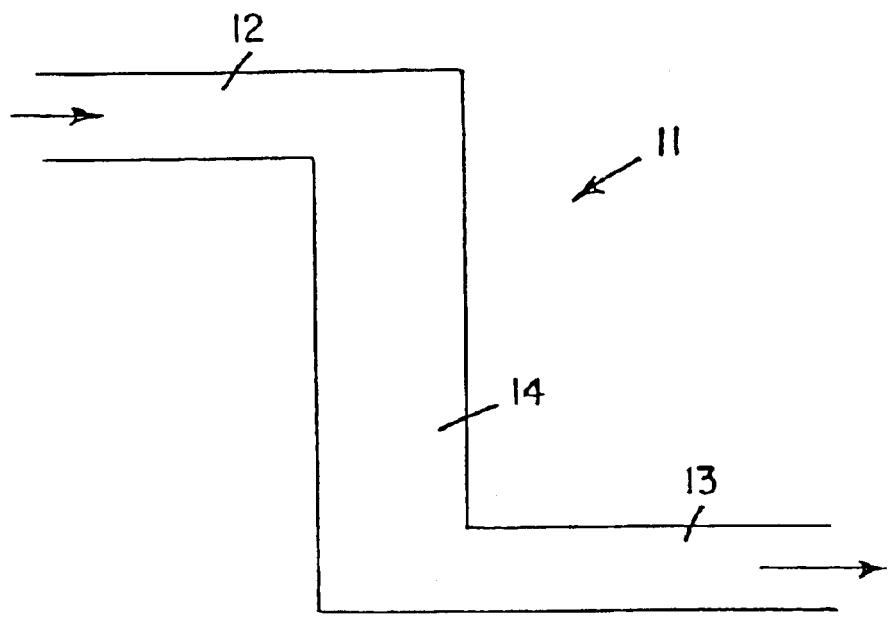
(PRIOR ART) FIG. 1
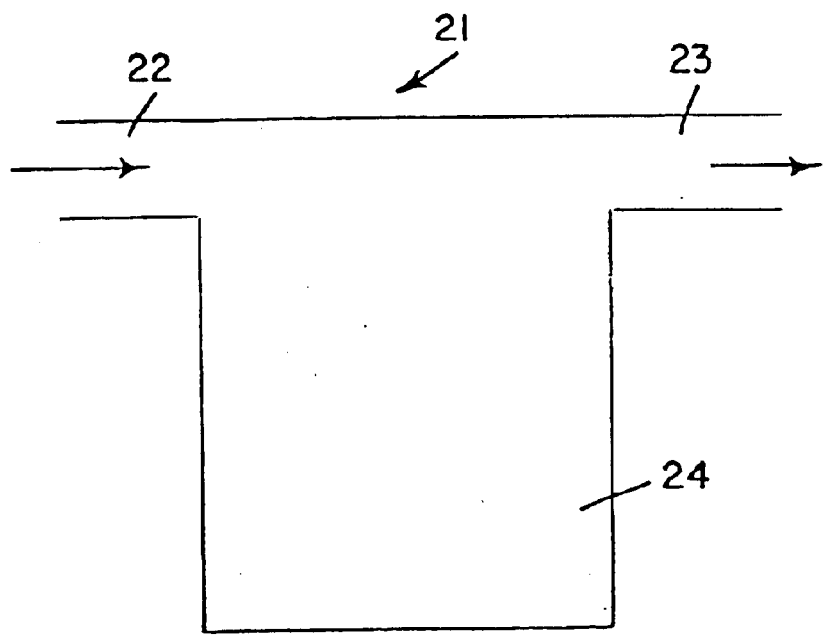
(PRIOR ART) FIG. 2

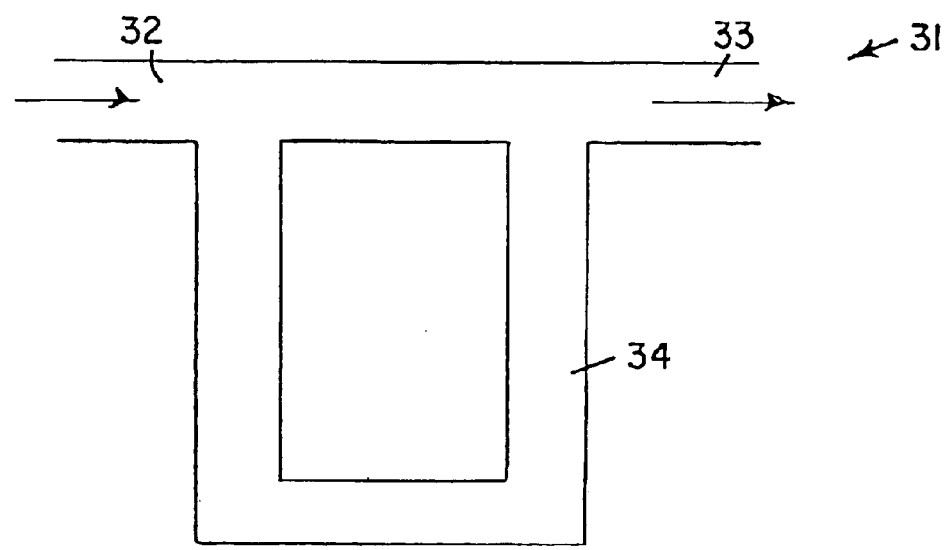
(PRIOR ART) FIG. 3
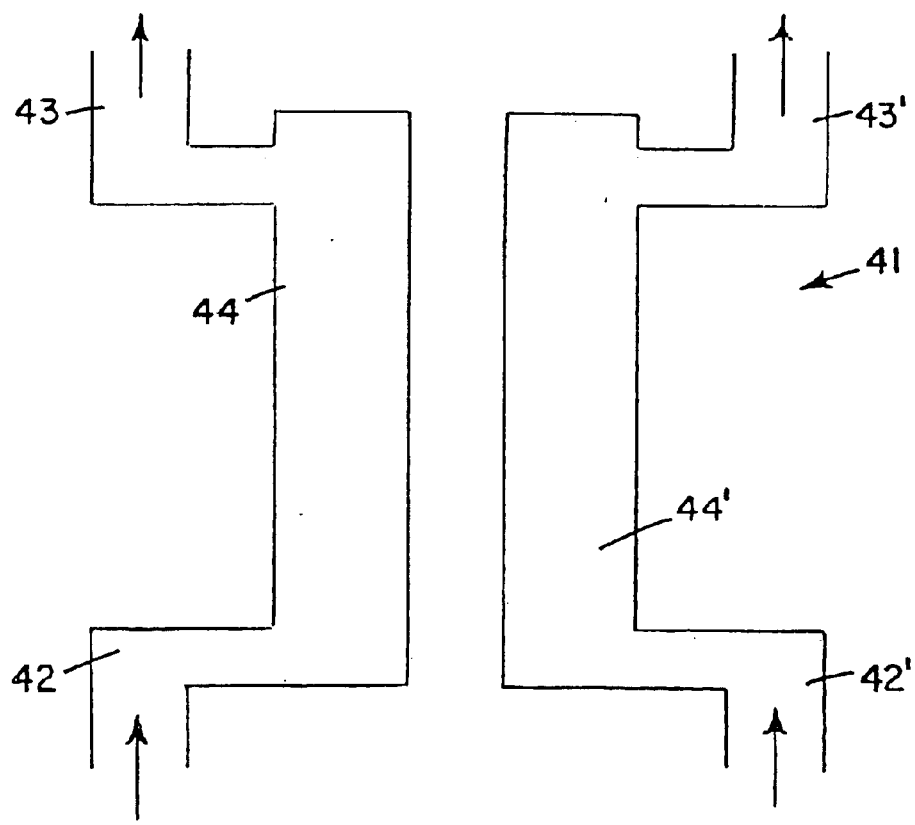
(PRIOR ART) FIG. 4

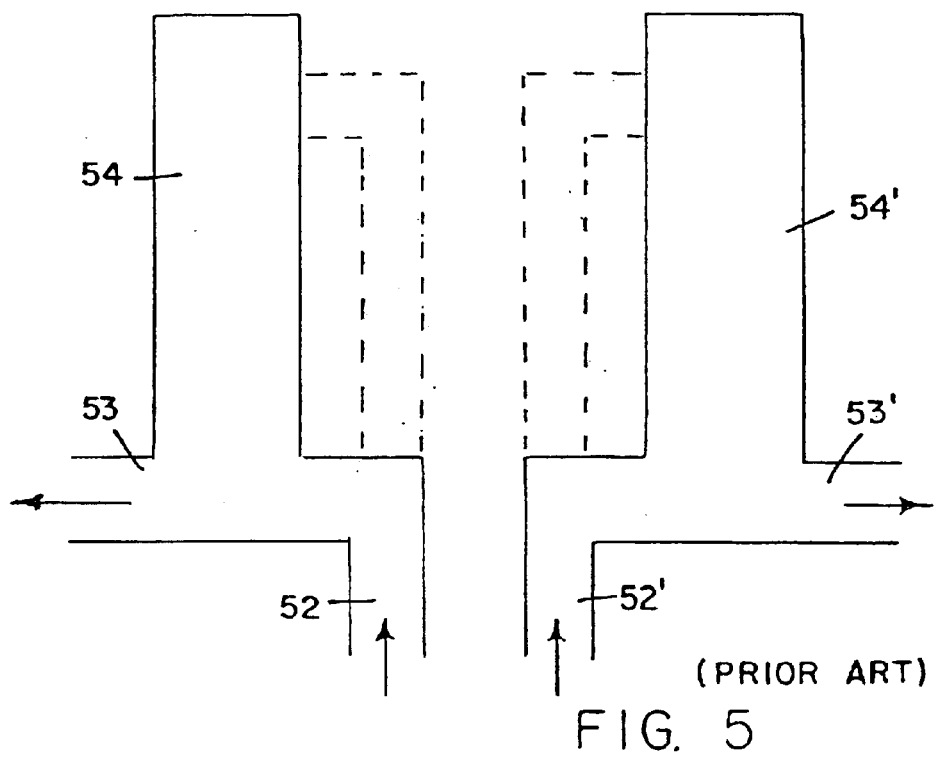
(PRIOR ART)
FIG. 5
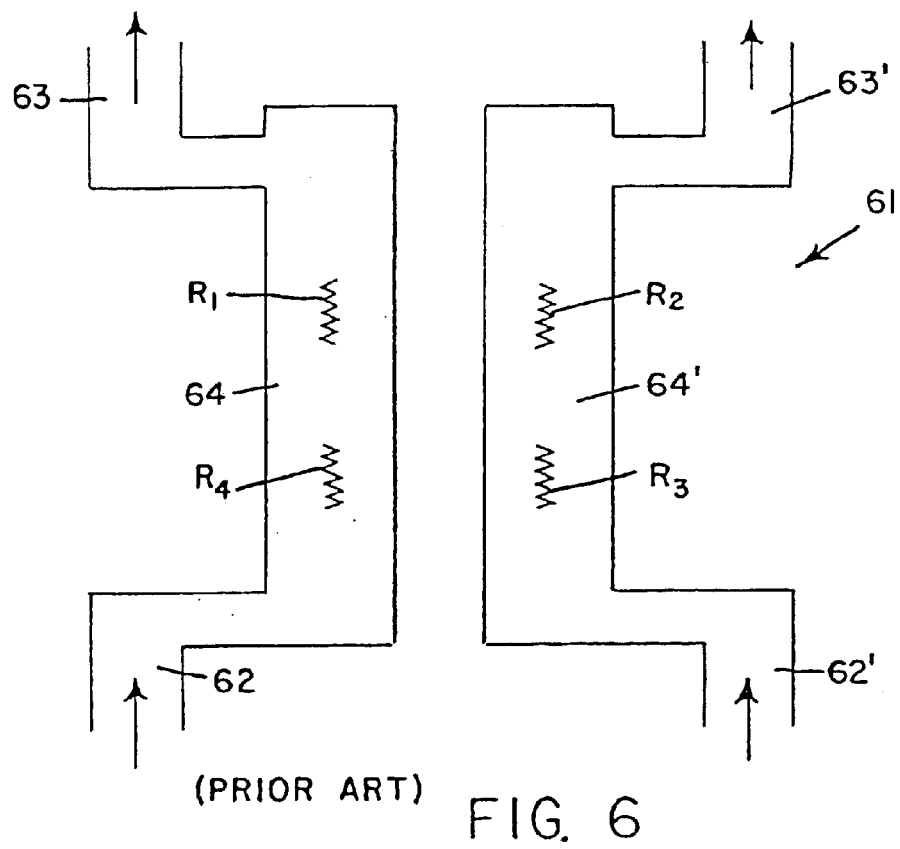
(PRIOR ART) FIG. 6

| | SENSITIVITY | RESPONSE | STABILITY | INTERFERENCE |
|---|---|---|---|---|
| DIRECT-TYPE | HIGH | QUICK | POOR | HIGH |
| DIFFUSED-TYPE | LOW | SLOW | GOOD | LOW |
| SEMI-DIFFUSED-TYPE | MEDIUM | MEDIUM | MEDIUM | MEDIUM |
| DESCRIBED DESIGN | HIGH | QUICK | GOOD | LOW |

APPARATUS AND METHOD FOR THERMAL CONDUCTIVITY DETECTION IN GAS CHOMATOGRAPHY EQUIPMENT

FIELD OF THE INVENTION

The present invention relates to thermal conductivity detectors used in gas chromatography applications.

BACKGROUND OF THE INVENTION

Gas chromatography involves vaporizing an analytic sample and injecting the vaporized sample onto a head of a chromatographic column. The vaporized sample is transported through the chromatographic column by a flow of an inert gas. A detector is then used to determine different components of the sample.

Various types of detectors can be used with gas chromatography equipment, and each type has particular advantages and disadvantages. One type of detector is a thermal conductivity detector, which for convenience is referred to hereinafter as a TCD. A TCD operates based on relative changes in the thermal conductivity of gas flowing through separate sample and reference cells of the TCD.

TCD's are valued for their relative simplicity, their relatively large linear dynamic range, and their general response to both organic and inorganic species. TCD's are also non-destructive, which permits collection of solutes after detection. TCD's are, however, often not as sensitive as other types of detectors. This limitation of existing TCD designs restricts the use of TCD's in some instances.

A TCD typically contains, in the sample and reference cells, pairs of electrically heated filaments whose temperature at constant electrical power depends upon the thermal conductivity of the surrounding gas. As carrier gas containing solutes passes through the cell, a change in the filament current occurs due to a change in the temperature of the filament. A comparison is made of current in a sample cell and current in a reference cell. A signal is generated from the measured difference. The resistances of the filament pairs are usually compared by incorporating them into two arms of a Wheatstone bridge circuit.

This Wheatstone bridge circuit is intended to amplify resistance changes due to analytes passing over the sample thermo-conductors, while disregarding changes in resistance that both sets of detectors produce due to flow rate fluctuations, etc. Two pairs of elements are used. One pair of elements is located in the flow of the effluent gas in the chromatographic column, and the other pair is located in the gas stream ahead of a sample injection chamber.

Direct-type designs provide favorable sensitivity, but at the expense of unfavorable stability and interference. By contrast, diffused-type designs are unfavorably diminished in sensitivity and response, but have favorably improved stability and interference characteristics. Accordingly, direct-type or diffused-type designs are selected for particular applications depending on which characteristics are important.

In practice, random gas flow fluctuations in gas chromatographic equipment adversely affect the performance of TCD. Such fluctuations affect direct-type designs more adversely than diffuse-type designs. In both cases, though, the quality of detected results deteriorates.

What is needed is a TCD design that has improved sensitivity, quick response time, good stability, and lower interference which enables it to be used in applications for which TCD have, heretofore, been unsuitable.

SUMMARY OF THE INVENTION

One feature of the present invention is to provide a thermal conductivity detector with maximized sensitivity, quick response time, good stability, and lower interference.

Another feature of the present invention is to minimize interference caused by flow fluctuations in a TCD design, while not substantially weakening the output signal of the TCD.

A further feature of the present invention is to have a TCD design that provides desirable sensitivity and response characteristics typical of direct-type TCD designs, combined with desirable stability and reduced interference characteristics typical of diffused-type TCD designs.

In accordance with one embodiment of the present invention, a thermal conductivity detector includes separate sample gas and reference gas chambers. Each chamber has a gas inlet, a gas outlet and a sensor. At least one passageway permits gas communication between the sample chamber and the reference chamber. For example, a passageway extends from the sample gas chamber to the reference gas chamber adjacent the gas inlets. As a further example, an additional connecting passageway may be provided adjacent the gas outlets. More specifically, an exhaust passageway extends from the first passageway to the additional passageway and there is an exhaust outlet connected to the additional passageway.

BRIEF DESCRIPTION OF THE DRAWINGS

FIG. 1 is a schematic representation of a prior art direct-type TCD design;

FIG. 2 is a schematic representation of a prior art diffused-type TCD design;

FIG. 3. is schematic representation of a prior art semi-diffused-type TCD design;

FIG. 4 is a schematic representation of a prior art direct-type TCD implementation;

FIG. 5 is a schematic representation of a prior art diffused-type and semi-diffused-type implementation;

FIG. 6 is a schematic representation of the TCD implementation of FIG. 4, which indicates filament detector placement.

DETAILED DESCRIPTION

Figure 7:
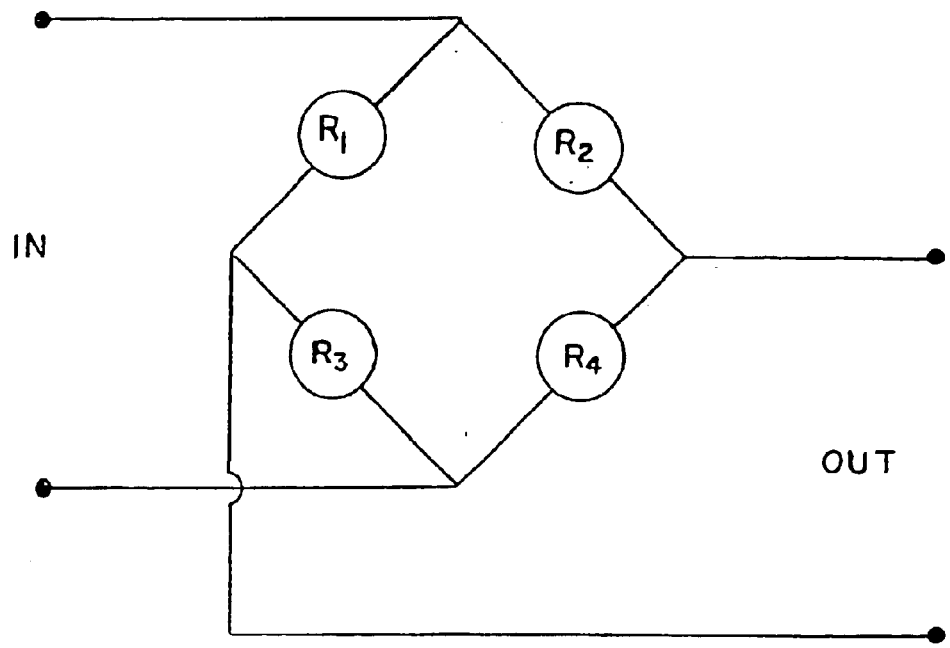
FIG. 7 is a schematic representation of bridge circuitry used to compare outputs from each of the filament detectors represented in FIG. 6.

FIGS. 1 to 3 represent existing TCD designs that can be used with gas chromatographic equipment. Each design is used in a pair, as represented in FIGS. 4 and 5.

Referring to FIG. 1, a prior art direct-type TCD design 11 has an input end 12 and an output end 13. A detecting portion 14 is located between the input end 12 and output end 13. FIG. 2 shows a prior art diffused-type TCD design 21. FIG. 3 shows a prior art semi-diffused-type TCD design 31, which is essentially a hybrid of the direct-type and diffused-type designs of FIGS. 1 and 2.

In the case of FIG. 1, gas flows directly past the detecting portion 14. In FIG. 2, by contrast, the main detecting portion 24 is adjacent the direct path from the input end 22 to the output end 23. Accordingly, the detecting portion 24 detects gas, which diffuses from this main path.

In FIG. 3, gas that diffuses from the main path between an input end 32 and an output end 33 flows directly past the directing portion 34.

FIG. 4 schematically represents two direct-type TCD designs of the kind represented in FIG. 1. FIG. 5, by contrast, schematically represents two diffused-type or semi-diffused-type TCD designs of the kind represented in FIGS. 2 and 3 respectively. In FIG. 5, the solid lines represent a diffused-type TCD design, and the dotted lines further represent a semi-diffused-type TCD design.

In FIGS. 4 and 5, the two back-to-back chambers respectively represent sample and reference chambers. The sample chambers are depicted on the left-hand side of these drawings, and are indicated by the reference numerals 44 in FIG. 4 and 54 in FIG. 5. The reference chambers are depicted in the right-hand side of the drawings, and are indicated by the reference numerals 44' in FIG. 4 and 54' in FIG. 5.

The sample chambers 44 and 54 are essentially the same in construction as the reference chambers 44' and 54'. Corresponding reference numerals are used to indicate corresponding features. The sample chambers 44 and 54 have inlets 42 and 52, respectively, and outlets 43 and 53, respectively. Correspondingly, the reference chambers 44' and 54' also have inlets 42' and 52', respectively, and outlets 43' and 53', respectively. Direct gaseous communication exists between matching inlets, chambers and outlets. There is no gaseous communication between the sample chambers 44 and 54 and the reference chambers 44' and 54', respectively, in the arrangements depicted in FIGS. 4 and 5.

Sample and reference gas streams respectively pass through sample chambers 44 and 54 and reference chambers 44' and 54' via the inlets, chambers and outlets in the direction indicated by arrowheads in FIGS. 4 and 5. As noted, there is no gaseous communication between the sample chambers 44 and 54 and the reference chambers 44' and 54', respectively.

In FIGS. 4 and 5, outputs from respective sample and reference gas streams are compared using an electrical bridge (as later described with reference to FIGS. 6 and 7) that amplifies differences in resistance and disregards common fluctuations in resistance.

FIGS. 6 and 7 represent how these changes in resistance are detected for the example of a direct-type TCD design, such as that provided by FIG. 4. Electrical filaments $R_1$, $R_2$, $R_3$ and $R_4$ are represented in each detecting portion 64, 64' to detect changes in electrical resistance that are caused by fluctuations in the gas stream that flows past the filaments.

FIG. 7 schematically represents each filament of FIG. 6 in a Wheatstone bridge configuration. Corresponding reference numerals are given to corresponding filaments. The Wheatstone bridge is an electrical bridge circuit used to measure resistance. In this case, the Wheatstone bridge circuitry of FIG. 7 in effect amplifies differences disregarding common fluctuations between the $R_1$ and $R_4$ filament pair, and $R_2$ and $R_3$ filament pair.

Figure 8:
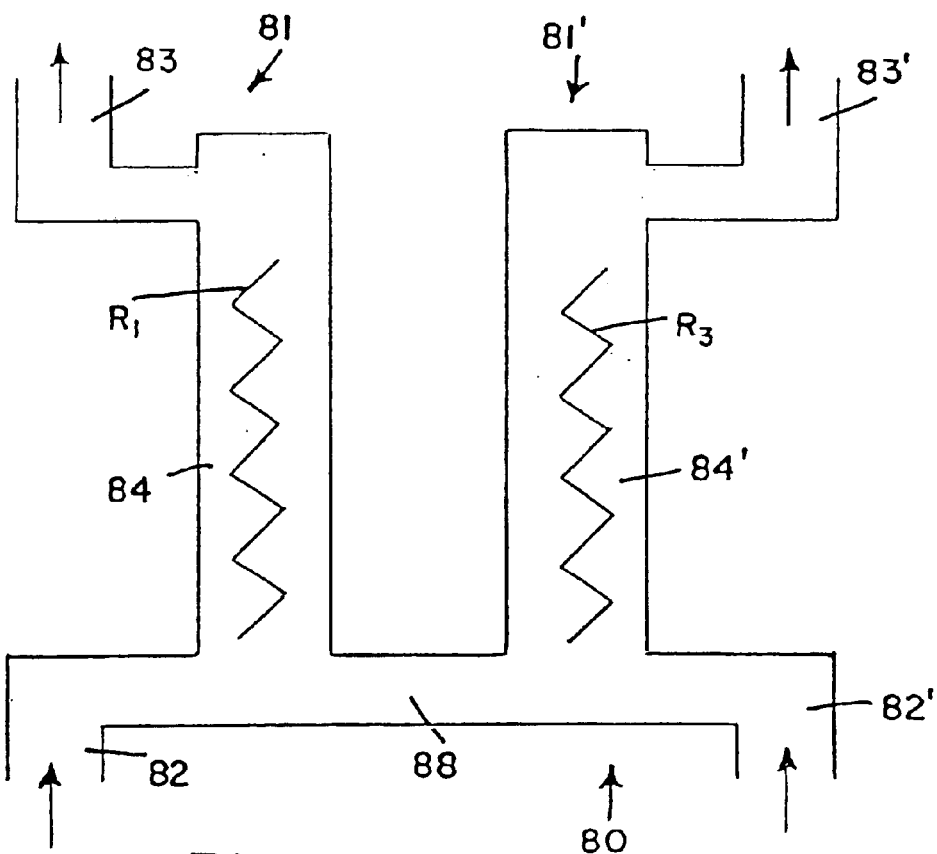
FIG. 8 is a schematic representation of a first TCD design embodying the principles of the present invention.
Figures 9, 10:
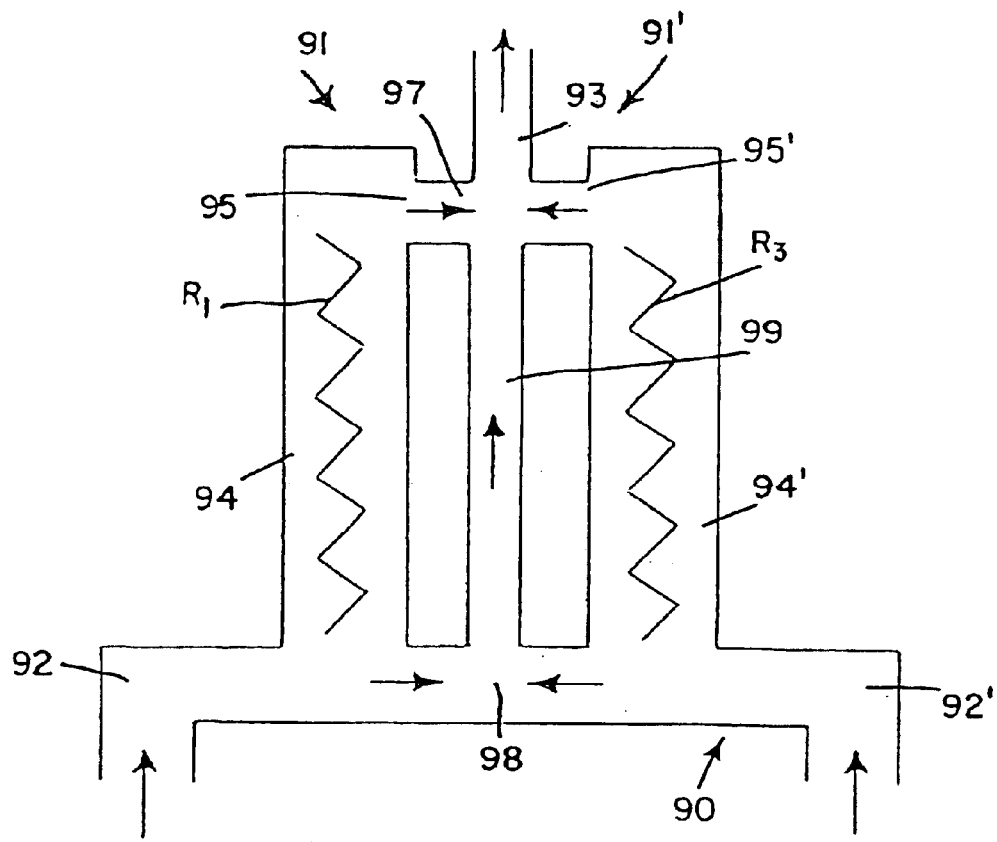
FIG. 9 is a schematic representation of a second TCD design embodying the principles of the present invention.
FIG. 10 is a table comparing the performance characteristics of the TCD designs of the present invention with those of prior art TCD designs.

FIGS. 8 and 9 illustrate two separate thermal conductivity detector designs (i.e., the detectors 80 and 90) in accordance with embodiments of the present invention. Both of the designs of FIGS. 8 and 9 are supported by the Wheatstone bridge of FIG. 7.

As will be described in more detail below, the detector of the present invention includes separate sample gas and reference gas chambers. Each chamber has a gas inlet, a gas outlet and a sensor. The chambers are connected by at least one passageway. In one embodiment of the invention, a passageway extends from the sample gas chamber and the reference gas chamber adjacent the gas inlets. In another embodiment of the invention, there is an additional connecting passageway adjacent the gas outlets. More specifically, an exhaust passageway extends from the first passageway to the additional passageway and there is an exhaust outlet connected to the additional passageway.

The structure in both embodiments of the invention assist in counterbalancing flow fluctuations in the TCD. Interference caused by flow fluctuations can be minimized, while not substantially weakening the output signal. The TCD designs of the present invention can provide desirable sensitivity and response characteristics typical of direct-type TCD designs, combined with desirable stability and reduced interference characteristics typical of diffused-type TCD designs.

A first design, generally indicated by the reference numeral 80 of FIG. 8 is referred to as a parallel direct-type design. The design of FIG. 8 includes a conduit or passageway 88 that connects respective gas inlets 82, 82' of a sample and reference gas chambers 84 and 84', respectively. The sample gas unit is generally indicated by the reference numeral 81, and a reference gas unit is, generally indicated by the reference numeral 81'.

Inlets 82 and 82' lead to the common conduit or gas passageway 88, to which sample and reference chambers 84 and 84', respectively, are connected. The sample and reference chambers 84 and 84', respectively, are, in turn, connected to respective outlets 83 and 83'. The passageway 88 supports a flow of gas between sample and reference gas streams that is required to equalize pressures between these two input gas streams. In this manner, the effect of spurious fluctuations of pressure in the sample or reference gas streams can be minimized at the electrical filaments $R_1$ and $R_3$.

Other un-described features of the detector 80 shown in FIG. 8 resemble the corresponding features of the design of FIG. 4, which will not be described in more detail hereinafter.

A second design, generally indicated by the reference numeral 90 of FIG. 9 is referred to as a "parallel half-diffused-type" design. The sample cell, generally indicated by the reference numeral 91, includes a sample gas chamber 94 that has a sample gas inlet 92 and a sample gas outlet 95. The reference cell, generally indicated by the reference numeral 91', includes a reference gas chamber 94' that has a reference gas inlet 92' and a reference gas outlet 95'. The design of FIG. 9 includes two conduits or gas passageways 98 and 97 between the sample cell 91, and the reference cell 91', at opposite ends of the cells 91, and 91' as represented in FIG. 9. There is also a common passageway 99, extending between the gas passageways 98 and 97, as well as an exhaust outlet 93 leading directly from passageway 97. The general direction in gas flow is represented by the arrowheads.

Accordingly, the chambers 94 and 94', the two gas passageways 98 and 97, and the common passageway 99, form a connecting grid of passageways from which gas from the inlets 92, 92' flows to the exhaust outlet 93. Again, as with the design depicted in FIG. 8, the effect of spurious gas pressure fluctuations in the sample and reference gas streams is minimized by the connecting passages to stabilize any gas pressure differentials that may exist. Sample gas chamber 94 contains an electrical filament $R_1$. Reference gas chamber 94' contains an electrical filament $R_3$.

In both FIGS. 8 and 9, the conduits minimize the effects of gas flow fluctuations on the performance of the TCD design, without substantially influencing the sensitivity and response speed.

For both designs, any change in gas volume of either the reference cell or the sample cell causes a corresponding change in the gas volume of the other cell. These changes are also reflected in the outputs of the filament detectors $R_1$, $R_3$. For the designs of FIGS. 8 and 9, $R_2$ and $R_4$ are not depicted in FIGS. 8 or 9, but are equal resistances used in the Wheatstone bridge circuitry of FIG. 7. In accordance with the operation of the Wheatstone bridge circuitry of FIG. 7, the output signal remains substantially the same in the face of spurious fluctuations.

Thus, the TCD designs represented in FIGS. 8 and 9 effectively counterbalance flow fluctuations, thereby minimizing flow fluctuation interferences at the output signal without weakening the output signal when sample flows through. The advantages of the TCD designs of the present invention relative to prior art TCD designs are shown graphically in FIG. 10. FIG. 10 also shows the relative limitations of the three existing TCD designs that are shown in FIGS. 1–3.

What is claimed is:

1. A thermal conductivity detector, comprising:
   (a) a sample gas chamber having a sample gas inlet and a sample gas outlet;
   (b) a reference gas chamber having a reference gas inlet and a reference gas outlet;
   (c) at least one passageway that permits gas communication between said sample gas chamber and said reference gas chamber, wherein said passageway extends from said sample gas inlet to said reference gas inlet;
   (d) a first sensor in said sample gas chamber; and
   (e) a second sensor in said reference gas chamber.

2. The detector as recited in claim 1, wherein each of said first sensor and second sensor is an electrical filament.

3. A thermal conductivity detector, comprising:
   (a) a sample gas chamber having a sample gas inlet and a sample gas outlet;
   (b) a reference gas chamber having a reference gas inlet and a reference gas outlet;
   (c) at least one passageway that permits gas communication between said sample gas chamber and said reference gas chamber, wherein the at least one passageway includes a first passageway that extends from said sample gas inlet to said reference gas inlet and a second passageway that extends from said sample gas outlet to said reference gas outlet;
   (d) a first sensor in said sample gas chamber; and
   (e) a second sensor in said reference gas chamber.

4. The detector as recited in claim 3, further comprising an exhaust passageway that extends from first passageway to said second passageway.

5. The detector as recited in claim 4, further comprising an exhaust outlet connected to said exhaust passageway.

6. A method for detecting gas using thermal conductivity, comprising:
   (a) providing a sample gas to a sample gas inlet of a sample chamber having a sample gas outlet and containing a first sensor;
   (b) providing a reference gas to a reference gas inlet of a reference gas chamber having a reference gas outlet and containing a second sensor;
   (c) causing said sample gas to flow past said first sensor;
   (d) causing said reference gas to flow past said second sensor; and
   (e) creating a gas communication between said sample chamber and said reference chamber, wherein said gas communication includes (1) a first gas communication between said sample chamber and said reference chamber adjacent said sample gas inlet and said reference gas inlet and (2) a second gas communication between said sample chamber and said reference chamber adjacent said sample gas outlet and said reference gas outlet.

7. The method as recited in claim 6, further comprising creating a gas communication between said sample gas chamber and said reference gas chamber from said first gas communication to said second gas communication.

8. The method as recited in claim 7, further comprising creating an exhaust gas flow said second gas communication.

* * * * *